United States Patent [19]

Clough et al.

[11] Patent Number: 5,395,837
[45] Date of Patent: * Mar. 7, 1995

[54] FUNGICIDES

[75] Inventors: John M. Clough, Marlow; Christopher R. A. Godfrey, Bracknell; Streeting: Ian T., Wokingham; Rex Cheetham, Bracknell, all of Great Britain

[73] Assignee: Zeneca Limited, London, England

[*] Notice: The portion of the term of this patent subsequent to Sep. 8, 2009 has been disclaimed.

[21] Appl. No.: 113,232

[22] Filed: Aug. 30, 1993

Related U.S. Application Data

[60] Continuation of Ser. No. 900,267, Jul. 20, 1992, Pat. No. 5,264,400, which is a division of Ser. No. 818,431, Dec. 27, 1991, Pat. No. 5,145,856, which is a continuation of Ser. No. 478,403, Feb. 12, 1990, abandoned.

[30] Foreign Application Priority Data

Feb. 10, 1989 [GB] United Kingdom ............... 8903019

[51] Int. Cl.$^6$ ................... C07D 239/52; A01N 43/54
[52] U.S. Cl. ..................... 514/269; 544/319
[58] Field of Search .................. 544/319; 514/269

[56] References Cited

U.S. PATENT DOCUMENTS

| | | | |
|---|---|---|---|
| 4,248,618 | 2/1981 | Serban et al. | 71/92 |
| 4,709,078 | 11/1987 | Schirmer et al. | 560/60 |
| 4,822,908 | 4/1989 | Kerbach et al. | 560/60 |
| 4,826,531 | 5/1989 | Anthony et al. | 71/94 |
| 4,863,503 | 9/1989 | Anthony et al. | 71/90 |
| 5,124,329 | 6/1992 | Clough et al. | 544/218 |

FOREIGN PATENT DOCUMENTS

| | | |
|---|---|---|
| 0178826 | 4/1986 | European Pat. Off. . |
| 0260794 | 8/1986 | European Pat. Off. . |
| 0242070 | 10/1987 | European Pat. Off. . |
| 0242081 | 10/1987 | European Pat. Off. . |
| 7906465 | of 0000 | South Africa . |
| 2193495 | 2/1988 | United Kingdom . |

Primary Examiner—John M. Ford
Attorney, Agent, or Firm—Cushman Darby & Cushman

[57] ABSTRACT

Compounds having the formula (I):

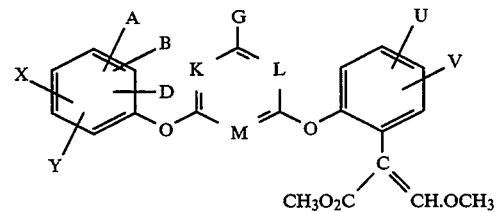

wherein the variables are herinbelow defined in the specification.

The compounds are useful as fungicides.

6 Claims, No Drawings

FUNGICIDES

This is a continuation of application Ser. No. 07/900,267, filed Jul. 20, 1992, now U.S. Pat. No. 5,264,440, and a division of Ser. No. 07/818,431, filed Dec. 27, 1991, now U.S. Pat. No. 5,145,856, which is a continuation of Ser. No. 07/478,403, filed Feb. 12, 1990, now abandoned.

This invention relates to derivatives of propenoic acid useful as fungicides, to processes for preparing them, to fungicidal compositions containing them, and to methods of using them to combat fungi, especially fungal infections of plants.

A range of pesticidal alkyl 2-(substituted)pyridinyl- and pyrimidinyloxyphenyl-3-alkoxypropenoates is described in EP-A-0242081.

According to the present invention there are provided pyrimidines having the formula (I):

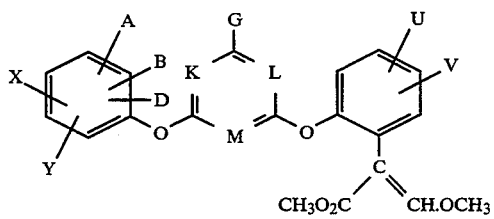

in which any two of K, L and M are nitrogen and the other is CE; X and Y are independently hydrogen, halogen, $C_{1-4}$ alkyl, $C_{3-6}$ cycloalkyl, $C_{2-4}$ alkenyl, $C_{2-4}$ alkynyl, $C_{2-4}$ alkynyloxy, phenyl, benzyloxy, cyano, isocyano, isothiocyanato, nitro $NR^1R^2$, $NR^1OR^2$, $N_3$, $NHCOR^1$, $NR^1CO_2R^2$, $NHCONR^1R^2$, $N=CHNR^1R^2$, $NHSO_2R^1$, $OR^1$, $OCOR^1$, $OSO_2R^1$, $SR^1$, $SOR^1$, $SO_2R^1$, $SO_2OR^1$, $SO_2NR^1R^2$, $COR^1$, $CR^1=NOR^2$, $CHR^1CO_2R^2$, $CO_2R^1$, $CONR^1R^2$, $CSNR^1R^2$, $CH_3O_2C.C:CH.OCH_3$, 1-(imidazol-1-yl)vinyl, a 5-membered heterocyclic ring containing one, two or three nitrogen heteroatoms, or a 5- or 6-membered heterocyclic ring containing one or two oxygen or sulphur heteroatoms, optionally a nitrogen heteroatom and optionally one or two oxo or thioxo substituents; or X and Y, when ortho to one another, join to form a 5- or 6-membered aliphatic or aromatic ring optionally containing one or two oxygen, sulphur or nitrogen atoms or one, two or three nitrogen atoms; A, B, D, E, G, U and V are independently hydrogen, halogen (especially fluorine and chlorine), $C_{1-4}$ alkyl. (especially methyl), $C_{1-4}$ alkoxy (especially methoxy), cyano, nitro or trifluoromethyl; and $R^1$ and $R^2$ are independently hydrogen, $C_{1-4}$ alkyl, $C_{2-4}$ alkenyl or phenyl; the aliphatic moieties of any of the foregoing being optionally substituted with one or more of halogen, cyano, $OR^1$, $SR^1$, $NR^1R^2$, $SiR^1_3$ or $OCOR^1$ and the phenyl moieties of any of the foregoing being optionally substituted with one or more of halogen, $C_{1-4}$ alkyl, $C_{1-4}$ alkoxy, nitro or cyano.

Because of the unsymmetrically substituted double bond of the propenoate group, the compounds of the invention may be obtained in the form of mixtures of (E) and (Z) geometric isomers. However, these mixtures can be separated into individual isomers, and this invention embraces such isomers and mixtures thereof in all proportions including those which consist substantially of the (Z)-isomer and those which consist substantially of the (E)-isomer.

The (E)-isomer, in which the groups $—CO_2CH_3$ and $—OCH_3$ are on opposite sides of the olefinic bond of the propenoate group, are the more fungicidally active and form a preferred embodiment of the invention.

Alkyl groups contain from 1 to 4 carbon atoms and may be in the form of straight or branched chains. Examples are methyl, ethyl, iso-propyl, n-butyl and t-butyl. Cycloalkyl groups contain from 3 to 6 carbon atoms and include cyclopropyl and cyclohexyl.

Alkenyl and alkynyl groups contain from 2 to 4 carbon atoms and may be in the form of straight or branched chains. Examples are ethenyl, allyl, methylallyl and propargyl.

Halogen is typically fluorine, chlorine or bromine.

Substituted aliphatic moieties include, in particular, halo($C_{1-4}$)alkyl, halo($C_{1-4}$)alkoxy, halo($C_{1-4}$)alkylthio, $CH_2OR^1$, $CH_2SR^1$ and $CH_2NR^1R^2$, wherein $R^1$ and $R^2$ are H, $C_{1-4}$ alkyl or phenyl.

Typical optional substituents of phenyl moieties are fluorine, chlorine, methyl, methoxy, nitro and cyano.

The ring

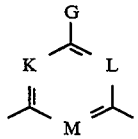

in formula (I) is a pyrimidine ring which may be joined to the phenoxy groups by any two of its ring carbon atoms adjacent to a ring nitrogen atom. Of particular interest are those compounds of formula (I) in which K and L are both nitrogen and M is CH. Typically, one or both of X and Y are hydrogen. When one of X and Y is not hydrogen it is preferably attached to the 2-position of the phenyl ring.

Thus, in one aspect, the invention provides compounds of formula (X) in which K, L and M have the meanings previously given; X, which is preferably attached to the 2-position of the phenyl ring, is hydrogen, halogen (e.g. fluorine, chlorine or bromine), $C_{1-4}$ alkyl (e.g. methyl or ethyl), $C_{1-4}$ alkyl (especially methyl) substituted with halogen (e.g. fluorine, chlorine or bromine), hydroxy, cyano, $C_{1-4}$ alkoxy (e.g. methoxy) or $C_{1-4}$ alkanoyloxy (e.g. acetoxy), $C_{2-4}$ alkenyl (e.g. ethenyl, allyl or methylallyl), $C_{2-4}$ alkynyl (e.g. ethynyl or propargyl), $C_{2-4}$ alkenyloxy (e.g. allyloxy), $C_{2-4}$ alkynyloxy (e.g. propargyloxy), phenyl, benzyl, cyano, isocyano, isothiocyanato, nitro, amino, mono- or di($C_{1-4}$)alkylamino (e.g. methylamino or dimethylamino), formyl amino, $C_{1-4}$ alkanoylamino (e.g. acetamido), benzylamino, ureido, phenylureido, $C_{1-4}$ alkylsulphonylamino (e.g. mesylamino), phenylsulphonylamino, hydroxy, $C_{1-4}$ alkoxy (e.g. methoxy or ethoxy), phenoxy, $C_{1-4}$ alkanoyloxy (e.g. acetoxy), $C_{1-4}$ alkylsulphonyloxy (e.g. mesyloxy), phenylsulphonyloxy, $C_{1-4}$ alkylthio (e.g. methylthio), $C_{1-4}$ alkylsulphinyl (e.g. methylsulphinyl), $C_{1-4}$ alkylsulphonyl (e.g. mesyl and n-butylsulphonyl), formyl, $C_{1-4}$ alkanoyl (e.g. acetyl), benzoyl, hydroxyimino($C_{1-4}$)alkyl (e.g. hydroxyiminomethyl), $C_{1-4}$ alkoxyimino($C_{1-4}$)alkyl (e.g. methoxyiminomethyl), carbamoyl, $C_{1-4}$ alkylcarbamoyl (e.g. methylcarbamoyl), thiocarbamoyl or $C_{1-4}$ alkylthiocarbamoyl (e.g. methylthiocarbamoyl), the phenyl ring of any of the foregoing being optionally substituted with halogen (e.g. fluorine or chlorine), $C_{1-4}$ alkyl (e.g. methyl), $C_{1-4}$ alkoxy (e.g. methoxy), nitro or cyano; and Y is halogen (e.g. fluorine or chlorine), $C_{1-4}$ alkyl (e.g. methyl), $C_{1-4}$ alkoxy (e.g. methoxy), nitro, cyano or preferably, hydrogen, or X and Y, when ortho to one another, together form methylenedioxy, or together with the phenyl ring to which they are attached form a naphthalene, quinoline, benzimidazole or benzothienyl ring.

In another aspect the invention provides compounds of the formula (I.1):

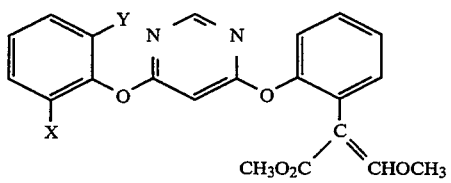

(I.1)

in which X is hydrogen, halogen (especially chlorine), $C_{1-4}$ alkyl (especially methyl), $C_{1-4}$ alkoxy (especially methoxy), trifluoromethyl, cyano, thiocarbamoyl or nitro, and Y is hydrogen or fluoro.

The invention is illustrated by the compounds listed in Tables I to III which follow. Throughout these Tables the methyl 3-methoxypropenoate group has the (E)-configuration and the substituents E, G, U and V are all hydrogen.

TABLE I

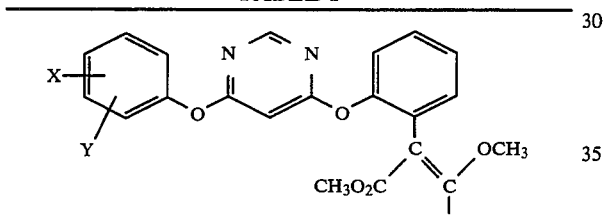

| Compound No. | X | Y | Melting point (°C.) | Olefinic* |
|---|---|---|---|---|
| 1 | H | H | glass | 7.46 |
| 2 | 2-F | H | gum | 7.47 |
| 3 | 3-F | H | gum | 7.47 |
| 4 | 4-F | H | 87–9 | 7.46 |
| 5 | 2-Cl | H | glass | 7.38 |
| 6 | 3-Cl | H | | |
| 7 | 4-Cl | H | | |
| 8 | 2-Br | H | glass | 7.42 |
| 9 | 2-Cyano | H | 118–119 | 7.50 |
| 10 | 3-Cyano | H | gum | 7.49 |
| 11 | 4-Cyano | H | gum | 7.49 |
| 12 | 2-Isocyano | H | | |
| 13 | 2-$NO_2$ | H | 120–121 | 7.52 |
| 14 | 3-$NO_2$ | H | gum | 7.49 |
| 15 | 4-$NO_2$ | H | gum | 7.48 |
| 16 | 2-$NH_2$ | H | gum | 7.46 |
| 17 | 3-$NH(CH_3)$ | H | | |
| 18 | 2-$N(CH_3)_2$ | H | | |
| 19 | 2-NH.CHO | H | | |
| 20 | 2-NH.$COCH_3$ | H | | |
| 21 | 3-NH.$COC_6H_5$ | H | | |
| 22 | 2-NH.$CONH_2$ | H | | |
| 23 | 3-NH.$CONH(C_2H_5)$ | H | | |
| 24 | 2-NH.$SO_2CH_3$ | H | | |
| 25 | 3-NH.$SO_2C_6H_5$ | H | | |
| 26 | 2-OH | H | 159–161 | 7.45 |
| 27 | 3-OH | H | | |
| 28 | 4-OH | H | | |
| 29 | 2-$OCH_3$ | H | gum | 7.49 |
| 30 | 3-$OCH_3$ | H | gum | 7.47 |
| 31 | 4-$OCH_3$ | H | 88–90 | 7.45 |
| 32 | 2-$OC_2H_5$ | H | glass | 7.46 |

TABLE I-continued

| | | | | |
|---|---|---|---|---|
| 33 | 3-(2-F—$C_6H_4O$) | H | | |
| 34 | 2-$OCOCH_3$ | H | gum | 7.47 |
| 35 | 2-$OSO_2CH_3$ | H | foam | 7.47 |
| 36 | 3-(4-$CH_3$—$C_6H_4SO_2O$) | H | | |
| 37 | 2-SCN | H | | |
| 38 | 3-SCN | H | | |
| 39 | 4-SCN | H | | |
| 40 | 2-$SCH_3$ | H | gum | 7.48 |
| 41 | 3-$SCH_3$ | H | | |
| 42 | 4-$SCH_3$ | H | | |
| 43 | 2-$S(O)CH_3$ | H | 135–6 | 7.48 |
| 44 | 2-$SO_2CH_3$ | H | 61–4 | 7.49 |
| 45 | 4-$SO_2(CH_2)_3CH_3$ | H | | |
| 46 | 2-CHO | H | foam | 7.50 |
| 47 | 3-CHO | H | | |
| 48 | 4-CHO | H | | |
| 49 | 2-$COCH_3$ | H | 99–101 | 7.42 |
| 50 | 3-$COC_6H_5$ | H | | |
| 51 | 2-(E)-CH:NOH | H | 146–7 | 7.45 |
| 52 | 3-(E)-CH:NOH | H | | |
| 53 | 4-(E)-CH:NOH | H | | |
| 54 | 2-(E)-CH:$NOCH_3$ | H | | |
| 55 | 2-(E)-C($CH_3$):NOH | H | | |
| 56 | 2-$CONH_2$ | H | | |
| 57 | 3-$CONH(CH_3)$ | H | | |
| 58 | 4-$CON(CH_3)_2$ | H | | |
| 59 | 2-$CSNH_2$ | H | 131–3 | 7.49 |
| 60 | 2-$CSNH(CH_3)$ | H | gum | 7.48 |
| 61 | 2-$CH_3$ | H | gum | 7.47 |
| 62 | 3-$CH_3$ | H | 92–5 | 7.45 |
| 63 | 4-$CH_3$ | H | gum | 7.46 |
| 64 | 2-$C_2H_5$ | H | 60–2 | 7.47 |
| 65 | 2-$CH_2F$ | H | | |
| 66 | 2-$CH_2Br$ | H | | |
| 67 | 2-$CH_2Cl$ | H | | |
| 68 | 2-$CH_2CN$ | H | | |
| 69 | 2-$CH_2OH$ | H | | |
| 70 | 2-$CH_2OCH_3$ | H | | |
| 71 | 2-$CH_2OCOCH_3$ | H | | |
| 72 | 3-$CH_2CN$ | H | | |
| 73 | 4-$CH_2OH$ | H | | |
| 74 | 3-$CH_2OCH_3$ | H | | |
| 75 | 2-CH:$CH_2$ | H | | |
| 76 | 2-$CH_2$CH:$CH_2$ | H | gum | 7.47 |
| 77 | 2-C:CH | H | 66–8 | 7.46 |
| 78 | 2-$CH_2$C:CH | H | | |
| 79 | 3-$CH_2C(CH_3)$:$CH_2$ | H | | |
| 80 | 2-$OCH_2$CH:$CH_2$ | H | glass | 7.47 |
| 81 | 2-$OCH_2$C:CH | H | gum | 7.47 |
| 82 | 2-$C_6H_5$ | H | 55 | 7.40 |
| 83 | 3-$C_6H_5$ | H | | |
| 84 | 4-$C_6H_5$ | H | | |
| 85 | 2-$C_6H_5O$ | H | | |
| 86 | 3-$C_6H_5O$ | H | | |
| 87 | 4-$C_6H_5O$ | H | | |
| 88 | 2-(4-Cl—$C_6H_4O$) | H | | |
| 89 | 2-$C_6H_5CH_2O$ | H | | |
| 90 | 2-Cyano | 4-Cl | | |
| 91 | 2-$NO_2$ | 4-F | | |
| 92 | 2-Cl | 4-Cl | | |
| 93 | 2-$OCH_3$ | 3-$OCH_3$ | | |
| 94 | 2-Cyano | 5-Cl | | |
| 95 | 2-Cyano | 6-Cyano | | |
| 96 | 2-F | 5-Cl | | |
| 97 | 3-$OCH_3$ | 5-$OCH_3$ | | |
| 98 | 3-Cyano | 4-F | | |
| 99 | 2-$NO_2$ | 3-$OCH_3$ | | |
| 100 | 3-$OCH_3$ | 5-Cyano | | |
| 101 | 2-$CO_2CH_3$ | H | glass | 7.50 |
| 102 | 2-I | H | glass | 7.48 |
| 103 | 2-$CF_3$ | H | 99–101 | 7.48 |
| 104 | 2-i-$C_3H_7$ | H | 63–5 | 7.47 |
| 105 | 2-i-$C_3H_7O$ | H | glass | 7.47 |
| 106 | 2-F | 6-F | 87–8 | 7.49 |
| 107 | 2-F | 4-F | 92–4 | 7.48 |
| 108 | 2-F | 3-F | gum | 7.48 |
| 109 | 2-n-$C_3H_7O$ | H | gum | 7.46 |
| 110 | 2-n-$C_4H_9O$ | H | gum | 7.47 |
| 111 | 2-CH(OH)$CH_3$ | H | 50–3 | 7.46 |
| 112 | 2-t-$C_4H_9$ | H | gum | 7.47 |
| 113 | 2-s-$C_4H_9$ | H | gum | 7.47 |
| 114 | 2-n-$C_3H_7$ | H | gum | 7.47 |

TABLE I-continued

| | | | | |
|---|---|---|---|---|
| 115 | 2-(E/Z)-CH=CH(CH₃) | H | glass | 7.46[1] |
| 116 | 2-Cyano | 4-OCH₃ | gum | 7.50 |
| 117 | 2-Cyano | 5-OCH₃ | oil | 7.50 |
| 118 | 2-Cyano | 4-Cl | 78–82 | 7.50 |
| 119 | 2-Cyano | 5-N(C₂H₅)₂ | oil | 7.50 |
| 120 | 2-CONH₂ | H | 138–141 | 7.46 |
| 121 | 2-C:CSi(CH₃)₃ | H | gum | 7.46 |
| 122 | 2-F | 5-F | 100–101 | 7.48 |
| 123 | 2-(E)-CH₃O₂C.C:CH.OCH₃ | H | 130–131 | 7.45 |
| 124 | 3-F | 5-F | 68–70 | 7.47 |
| 125 | 2-NHOH | H | | |
| 126 | 2-CH₂OCH₃ | H | | |
| 127 | 2-CH₂CN | H | | |
| 128 | 2-N₃ | H | | |
| 129 | 2-Cyano | 6-F | | |
| 130 | 2-NO₂ | 6-F | | |
| 131 | 2-CSNH₂ | 6-F | | |
| 132 | 2-Cyano | 3-F | | |
| 133 | 2-Cyano | 5-F | | |
| 134 | 2-Cyano | 3-OCH₃ | | |
| 135 | 2-Cyano | 6-OCH₃ | | |
| 136 | 2-NO₂ | 4-CH₃ | | |
| 137 | 2-NO₂ | 5-OCH₃ | | |
| 138 | 2-NO₂ | 6-OCH₃ | | |
| 139 | 2-CSNH₂ | 3-OCH₃ | | |
| 140 | 2-CSNH₂ | 4-OCH₃ | | |
| 141 | 2-CSNH₂ | 5-OCH₃ | | |
| 142 | 2-CSNH₂ | 6-OCH₃ | | |
| 143 | 2-Cyano | 3-Cyano | | |
| 144 | 2-F | 3-Cyano | | |
| 144 | 2-OCH₃ | 3-Cyano | | |
| 145 | 3-Cyano | 6-F | | |
| 146 | 2-(3-methyl-isoxazol-5(4H)-one-yl) | H | | |
| 147 | 2-(4-methyl-1,2-dithiol-3-one-yl) | H | | |
| 148 | 2-(2-methyl-4,5-dihydrothiazol-yl) | H | | |
| 149 | 2-(2-methyl-1,3-oxazin-4,6-dione-yl) | H | | |
| 150 | 2-Cyano | 4-Br | | |
| 151 | 2-Cyano | 6-Br | | |
| 152 | 2-Cyano | 4-NO₂ | | |
| 153 | 2-Cyano | 6-NO₂ | | |
| 154 | 2-Cyano | 6-OC₂H₅ | | |
| 155 | 2-Cyano | 4-CO₂CH₃ | | |
| 156 | 2-Cyano | 6-CO₂C₂H₅ | | |
| 157 | 2-Cyano | 6-CH₃ | | |
| 158 | 2-Cyano | 5-CH₂C₆H₅ | | |
| 159 | 2-Cyano | 4-OCF₃ | | |
| 160 | 2-Cyano | 4-Cyano | | |

Structure: Ar—O—(pyrimidine)—O—(phenyl with C(CO₂CH₃)=CH(OCH₃) substituent)

| Compound No. | Ar | Melting point (°C.) | Olefinic* |
|---|---|---|---|
| 161 | 8-quinolinyl | 133–5 | 7.52 |
| 162 | 1-naphthyl | | |
| 163 | 2-naphthyl | | |
| 164 | 2,3-methylenedioxyphenyl | | |
| 165 | benzothiophen-7-yl | | |
| 166 | benzimidazol-4-yl (NH) | | |
| 167 | Pentafluorophenyl | | |
| 168 | 2,4,6-Tri-F—C₆H₂ | | |
| 169 | 2,3,5,6-Tetra-F—C₆H | | |
| 170 | 2,3,6-Tri-F—C₆H₂ | | |
| 171 | 2,3-Di-cyano-6-F—C₆H₂ | | |
| 172 | 2,6-Di-F-3-CH₃O—C₆H₂ | | |
| 173 | 2,6-Di-F-4-CH₃O—C₆H₂ | | |
| 174 | 2,6-Di-F-3-NO₂—C₆H₂ | | |
| 175 | 2,6-Di-F-4-NO₂—C₆H₂ | | |
| 176 | 2,6-Di-F-3,5-di-CH₃O—C₆H | | |
| 177 | 4,6-Di-Br-2-cyano-C₆H₂ | | |
| 178 | 3-Cyano-2,6-di-F—C₆H₂ | | |
| 179 | 6-Br-2-cyano-4-CH₃O—C₆H₂ | | |
| 180 | 6-Br-4-Cl-2-cyano-C₆H₂ | | |
| 181 | 6-Br-2-cyano-4-NO₂—C₆H₂ | | |
| 182 | 3-Br-2-cyano-6-CH₃O—C₆H₂ | | |
| 183 | 3,5-Di-Cl-2-cyano-C₆H₂ | | |
| 184 | 4,6-Di-Cl-2-cyano-C₆H₂ | | |
| 185 | 3-Br-2-cyano-4-CH₃O—C₆H₂ | | |
| 186 | 4-Br-2-cyano-6-NO₂—C₆H₂ | | |
| 187 | 4-Br-2-cyano-6-CH₃O—C₆H₂ | | |

TABLE I-continued

| | |
|---|---|
| 188 | 2-Cyano-4-I-6-CH$_3$O—C$_6$H$_2$ |
| 189 | 2-Cyano-6-CH$_3$O-4-NO$_2$—C$_6$H$_2$ |
| 190 | 2-Cyano-4,6-di-NO$_2$—C$_6$H$_2$ |
| 191 | 2-Cyano-4-CH$_3$-6-NO$_2$—C$_6$H$_2$ |
| 192 | 2-Cyano-4-CH$_3$O-6-NO$_2$—C$_6$H$_2$ |
| 193 | 2-Cyano-5,6-di-CH$_3$O—C$_6$H$_2$ |
| 194 | 2-Cyano-5,6-di-CH$_3$O-3-CH$_3$—C$_6$H |
| 195 | 3,4-Di-Br-2-cyano-6-CH$_3$O—C$_6$H |
| 196 | 3-Br-2-cyano-6-CH$_3$O-4-NO$_2$—C$_6$H |
| 197 | 2-Cyano-6-CH$_3$CH$_2$O-4-NO$_2$—C$_6$H$_2$ |

198

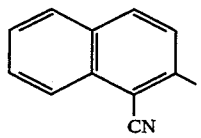

199

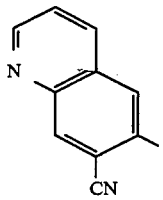

*Chemical shift of singlet from olefinic proton on beta-methoxypropenoate group (ppm from tetramethylsilane). Solvent: CDCl$_3$ unless otherwise stated.
[1]The ratio of the (E)- and (Z)-isomers of the prop-1-enyl group of compound No. 115 is either 2:1 or 1:2.

TABLE II

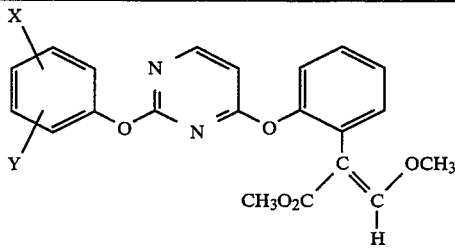

Table II comprises 199 compounds of the general structure above with all the values of X and Y listed in Table I. That is, compounds numbers 1 to 199 of Table II are the same as those of Table I except that the pyrimidine ring is 4,6-disubstituted in Table I and 2,4-disubstituted as shown in Table II.

| Compound No | X | Y | Melting Point (°C.) | Olefinic* |
|---|---|---|---|---|
| 1 | H | H | 114–115 | 7.46 |
| 123 | 2-(E)-CH$_3$O$_2$C.C:CH.OCH$_3$ | H | 60–70 | 7.44 and 7.47 |

*Chemical shift of singlet from olefinic proton on beta-methoxypropenoate group (ppm from tetramethylsilane). Solvent: CDCl$_3$ unless otherwise stated.

TABLE III

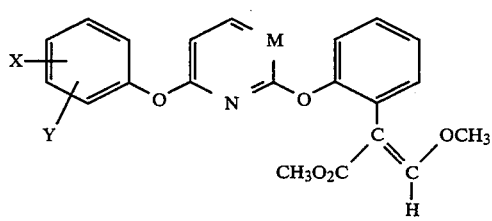

Table III comprises 199 compounds of the general structure above with all the values of X and Y listed in Table I. That is, compounds numbers 1 to 199 of Table III are the same as those of Table I except that the pyrimidine ring is 4,6-disubstituted in Table I and 2,4-disubstituted as shown in Table III.

| Compound No | X | Y | Melting Point (°C.) | Olefinic* |
|---|---|---|---|---|
| 1 | H | H | 96–97 | 7.42 |
| 9 | 2-Cyano | H | foam | 7.43 |

*Chemical shift of singlet from olefinic proton on beta-methoxypropenoate group (ppm from tetramethylsilane). Solvents CDCl$_3$ unless otherwise stated.

TABLE IV

Selected proton NMR data

Table IV shows selected proton NMR data for certain compounds described in Table I (except where otherwise indicated). Chemical shifts are measured in ppm from tetramethylsilane, and deuterochloroform was used as solvent. Unless otherwise stated, spectra were recorded on an instrument operating at 270 MHz. The following abbreviations are used:

| | |
|---|---|
| s = | singlet |
| d = | doublet |
| t = | triplet |
| m = | multiplet |
| q = | quartet |
| dd = | double doublet |
| br = | broad |
| ppm = | parts per million |

| Compound No | Proton NMR data |
|---|---|
| 1 | 3.60(3H, s); 3.75(3H, s); 6.23(1H, s); 7.10–7.50(9H, m); 7.46(1H, s); 8.43(1H, s)ppm |
| 2 | 3.60(3H, s); 3.74(3H, s); 6.32 (1H, s); 7.15–7.46(8H, m); 7.47 (1H, s); 8.40(1H, s)ppm |
| 3 | 3.63(3H, a); 3.76(3H, s); 6.27(1H, s); 6.86–7.03 (3H, m); 7.16–7.50(5H, m); 7.47(1H, s); 8.43(1H, s)ppm |
| 5 | 3.50(3H, s); 3.61(3H, s); 6.21(1H, s); 7.08–7.43(8H, m); 7.38(1H, s); 8.30 (1H, s)ppm |
| 8 | 3.54(3H, s); 3.68(3H, s); 6.23 (1H, a); 7.06–7.36(7H, m); 7.42 (1H, s); 7.59(1H, d); 8.33 (1H, s)ppm |
| 10 | 3.63(3H, s); 3.77(3H, s); 6.33 (1H, s); 7.20(1H, d); 7.25–7.60 (7H, m); 7.49(1H, s); 8.40(1H, s) ppm |
| 11 | 3.62(3H, s); 3.78(3H, s); 6.34 (1H, s); 7.20(1H, d); 7.25–7.45 (5H, m); 7.49(1H, s); 7.73(2H, d); 8.41(1H, s)ppm |
| 14 | 3.65(3H, s); 3.78(3H, s); 6.37 (1H, s); 7.08–7.65(6H, m); 7.49 (1H, s); 8.04(1H, t); 8.14(1H, dd); 8.41(1H, s)ppm |
| 15 | 3.64(3H, s); 3.78(3H, s); 6.39(1H, s); 7.20(1H, d); 7.26–7.46(5H, m); 7.48(1H, s); 8.32(2H, d); 8.42(1H, s)ppm |
| 16 | 3.60(3H, s); 3.74(3H, s); 3.74(2H, br s); 6.23(1H, s); 6.77–6.87(2H, m); 6.98–7.12(2H, m); 7.24–7.42(4H, m); 7.46(1H, s); 8.44(1H, s)ppm |
| 30 | 3.61(3H, s); 3.76(3H, s); 3.82 (3H, s); 6.23(1H, s); 6.68–6.75 (2H, m); 6.80(1H, dd); 7.19(1H, d); 7.25–7.42(4H, m); 7.47(1H, s); 8.43 (1H, s)ppm |
| 32 | 1.23(3H, t); 3.59(3H, s); 3.73 (3H, s); 4.02(2H, q); 6.25(1H, s); 7.00(2H, d); 7.46(1H, s); 8.39 (1H, s)ppm |
| 34 | 2.17(3H, s); 3.60(3H, s); 3.75 (3H, s); 6.29(1H, s); 7.18–7.43 (8H, m); 7.47(1H, s); 8.41(1H, s)ppm |
| 35 | 3.12(3H, s); 3.61(3H, s); 3.74 (3H, s); 6.29(1H, s); 7.19–7.50 |

TABLE IV-continued

| | |
|---|---|
| 40 | (8H, m); 7.47(1H, s); 8.40 (1H, s)ppm |
| 40 | 3.60(3H, s); 3.75(3H, s); 6.28 (1H, s); 7.09(1H, dd); 7.20–7.44 (7H, m); 7.48(1H, s); 8.42(1H, s) ppm |
| 46 | 3.63(3H, s); 3.77(3H, s); 6.39 (1H, s); 7.20–7.45(6H, m); 7.50 (1H, s); 7.68(1H, t); 7.97(1H, d); 8.39(1H, s)ppm |
| 61 | 2.17(3H, s); 3.60(3H, s); 3.75 (3H, s); 6.20(1H, s); 7.00–7.50 (8H, m); 7.48(1H, s); 8.42(1H, s)ppm |
| 63 | 2.37(3H, s); 3.59(3H, s); 3.73 (3H, s); 6.22(1H, s); 7.00(2H, d); 7.14–7.44(6H, m); 7.46(1H, s); 8.42(1H, s)ppm |
| 76 | 3.28–3.30(2H, d); 3.60(3H, s); 3.74 (3H, s); 4.98–5.02(1H, m); 5.05 (1H, s); 5.81–5.96(1H, m); 6.21 (1H, s); 7.04–7.08(1H, m); 7.18–7.42 (7H, m); 7.47(1H, s); 8.42(1H, s)ppm. |
| 80 | 3.59(3H, s); 3.73(3H, s); 4.51–4.53 (2H, m); 5.16–5.26(2H, m); 5.79–5.94 (1H, m); 6.25(1H, s); 6.98–7.03 (2H, m); 7.12–7.42(6H, m); 7.47 (1H, s); 8.39(1H, s)ppm |
| 81 | 2.48–2.50(1H, m); 3.60(3H, s); 3.74(3H, s); 3.65(2H, d); 6.24(1H, s); 7.03–7.43(8H, m); 7.47(1H, s); 8.40(1H, s)ppm |
| 101 | 3.62(3H, s); 3.75(3H, s); 3.76 (3H, s); 6.33(1H, s); 7.17–7.45 (6H, m); 7.50(1H, s); 7.57(1H, t); 8.03(1H, d); 8.36(1H, s)ppm |
| 102 | 3.62(3H, s); 3.76(3H, s); 6.31 (1H, s); 7.02(1H, t); 7.14–7.51(6H, m); 7.48(1H, s); 7.88(1H, d); 8.41(1H, s)ppm |
| 105 | 1.21(6H, d); 3.60(3H, s); 3.74(3H, s); 4.44–4.56(1H, m); 6.23(1H, s); 6.95–7.02(2H, m); 7.11–7.49(6H, m); 7.47(1H, s)ppm |
| 106 | 3.62(3H, s); 3.74(3H, s); 6.38(1H, s); 7.00(2H, t); 7.15–7.45(5H, m); 7.49(1H, s); 8.39(1H, s)ppm |
| 108 | 3.62(3H, s); 3.74(3H, s); 6.35 (1H, s); 6.95–7.43(7H, m); 7.48 (1H, s); 8.39(1H, s)ppm |
| 109 | 0.80(3H, t); 1.56–1.70(2H, m); 3.60(3H, s); 3.74(3H, s); 3.90 (2H, t); 6.24(1H, s); 6.98(2H, d); 7.10–7.42(6H, m); 7.46(1H, s); 8.39(1H, s) ppm |
| 110 | 0.86(3H, t); 1.18–1.30(2H, m); 1.56–1.64(2H, m); 3.60(3H, s); 3.74 (3H, s); 3.94(2H, t); 6.25(1H, s); 7.00(2H, d); 7.11–7.43(6H, m); 7.47(1H, s); 8.38(1H, s) ppm |
| 112 | 1.34(9H, s); 3.68(3H, s); 3.74(3H, s); 6.24(1H, s); 6.95–7.98(1H, m); 7.17–7.48(7H, m); 7.47(1H, s); 8.45 (1H, s)ppm |
| 113 | 0.79(3H, t); 1.16(3H, d); 1.49–1.67 (2H, m); 1.75–1.88(1H, m); 3.59(3H, s); 3.74(3H, s); 6.19(1H, s); 7.00–7.05 (1H, m); 7.18–7.46(7H, m); 7.47 (1H, s); 8.42(1H, s) ppm |
| 114 | 0.91(3H, t); 1.53–1.66(2H, m); 2.49(2H, t); 3.59(3H, s); 3.74 (3H, s); 6.20(1H, s); 7.00–7.04 (1H, m); 7.18–7.46(7H, m); 7.47 (1H, s); 8.41(1H, s)ppm |
| 115 | For both isomers: 1.76–1.85(3H, m); 3.58(3H, s); 3.73(3H, s); 7.00–7.42 (7H, m); 7.46(1H, s); 7.54–7.58 (1H, m)ppm For major isomer: 6.18(⅔H, s); 6.22–6.32(⅔H, m); 6.38(⅔H, br s); 8.42(⅔H, s)ppm. For minor isomer: 5.70–5.83(⅓H, m); 6.15(⅓H, s); 6.44(⅓H, br s); 8.39(⅓H, s)ppm |
| 116 | 3.63(3H, s); 3.75(3H, s); 3.85 (3H, s); 6.38(1H, s); 7.15–7.45 (7H, m); 7.50(1H, s); 8.40(1H, s)ppm |
| 117 | 3.63(3H, s); 3.75(3H, s); 3.86 (3H, s); 6.40(1H, s); 6.80(1H, s); 6.88(1H, d); 7.2–7.45(4H, m); 7.50 (1H, s); 7.61(1H, d); 8.41 (1H, s)ppm |
| 119 | 1.20(6H, t); 3.38(4H, q); 3.63 (3H, s); 3.74(3H, s); 6.35(1H, s); 6.40(1H, d); 6.52(1H, dd); 7.2–7.46 (5H, m); 7.50(1H, s); 8.43(1H, s) ppm |
| 121 | 0.10(9H, s); 3.61(3H, s); 3.74 (3H, s); 6.29(1H, s); 7.12–7.43 (7H, m); 7.46(1H, s); 7.50–7.55 (1H, m); 8.41(1H, s)ppm |
| 9 (Table III) | 3.57(3H, s); 3.68(3H, s); 6.75 (1H, d); 7.10–7.40(6H, m); 7.43 (1H, s); 7.59(1H, t); 7.68(1H, d); 8.40(1H, d)ppm |

The compounds of the invention of formula (I) [equivalent to (IA) when W is the group $CH_3O_2C.C=CH.OCH_3$] can be prepared by the steps illustrated in Schemes I and II. Throughout these Schemes the terms X, Y, A, B, D, G, U, V, K, L and M are as defined above; W is $CH_3O_2C.C=CH.OCH_3$ (or a group that can be transformed into $CH_3O_2C.C=CH.OCH_3$ using methods previously described in EP-A-0242081); $Z^1$ and $Z^2$, which may be the same or different, are leaving groups (such as halogen or $CH_3SO_2—$), $Z^1$ being the leaving group which is more readily displaced if both $Z^1$ and $Z^2$ are present in the same compound or if $Z^1$ and $Z^2$ are both present in different compounds of a coupling reaction; $T^1$ is hydrogen or a metal (such as sodium); and $T^2$ is hydrogen, a metal (such as sodium) or a protecting group (such as benzyl). Each reaction shown in Schemes I and II is performed either in a suitable solvent or without a solvent, and at a suitable temperature.

Thus compounds of the invention of formula [(IA): W is the group $CH_3O_2C.C=CH.OCH_3$] can be prepared by two successive reactions of the Ullmann type, using appropriately functionalised benzene and pyrimidine intermediates. The pathways shown in Schemes I and II illustrate that (i) the order of the steps by which these benzene and pyrimidine units are assembled can be varied; and (ii) the functional groups which react during the Ullmann coupling, namely an oxygen nucleophile and a leaving group on an aromatic ring, may be positioned on either of the substrates at each individual step.

For example, compounds of formula (IA) can be prepared from compounds of formula (II) by treatment with phenols of formula (III), wherein $T^1$ is hydrogen, in the presence of a base (such as potassium carbonate). Alternatively, compounds of formula (IA) can be prepared from compounds of formula (II) by treatment with phenolate salts of formula (III), wherein $T^1$ is a metal (such as sodium).

Compounds of formula (II) can be prepared by treatment of compounds of formula (IV) with phenols of formula (V), wherein $T^1$ is hydrogen, in the presence of a base (such as potassium carbonate). Alternatively, compounds of formula (II) can be prepared by treatment of compounds of formula (IV) with phenolate salts of formula (V), wherein $T^1$ is a metal (such as sodium). Similarly, compounds of formula (II) can be prepared by allowing compounds of formula (VI) to react with compounds of formula (VII); when $T^1$ is hydrogen, the reaction is performed in the presence of a base (such as potassium carbonate).

The preparation of compounds of formula (IA) from intermediates (VIII), (XI) and (XII), as well as the preparation of these intermediates from the monocyclic precursors, is carried out by similar methods.

Modifications to the group W may be made at any appropriate stage in the pathways shown in Schemes I and II. For example, during one or more of the Ullmann couplings, W may be the group $CH_2CO_2R$ (wherein R is H, $CH_3$ or a metal) to be converted at the last stages of the synthesis into the group $CH_3O_2C.C$=$CH.OCH_3$ using, for example, one of the methods described in EP-A-0242081. When $T^2$ is a protecting group, it may be removed at any appropriate reaction step. The substituents X, Y, A, B, D, E (one of K, L and M having the value CE, wherein E is as defined above), G, U and V may also be modified at any appropriate reaction step. For example, if X is $NO_2$ it may be converted via reduction and diazotisation into a halogen, CN or OH group, and this may be carried out on intermediates such as (XI) or (XII) or on the compounds of formula (IA). Or, for example, if G is a halogen such as chlorine, it may be removed at an appropriate stage of the synthesis (such as at the last stage) to give the corresponding pyrimidine in which G is hydrogen.

The intermediates of formulae (II) and (VIII) may be interconverted using standard methods. The intermediates of formulae (XI) and (XII) are similarly interconvertible. Compounds of formulae (III), (IV), (VI), (IX), (X), (XIII), (XIV), (XV), (XVI) and (XVII) can be prepared by standard methods described in the chemical literature. Compounds of formulae (V) and (VII) can either be prepared by standard methods described in the chemical literature, or, when W is $CH_3O_2C.C$=$CH.OCH_3$, can be prepared by methods described in EP-A-0242081 and EP-A-0178826 respectively.

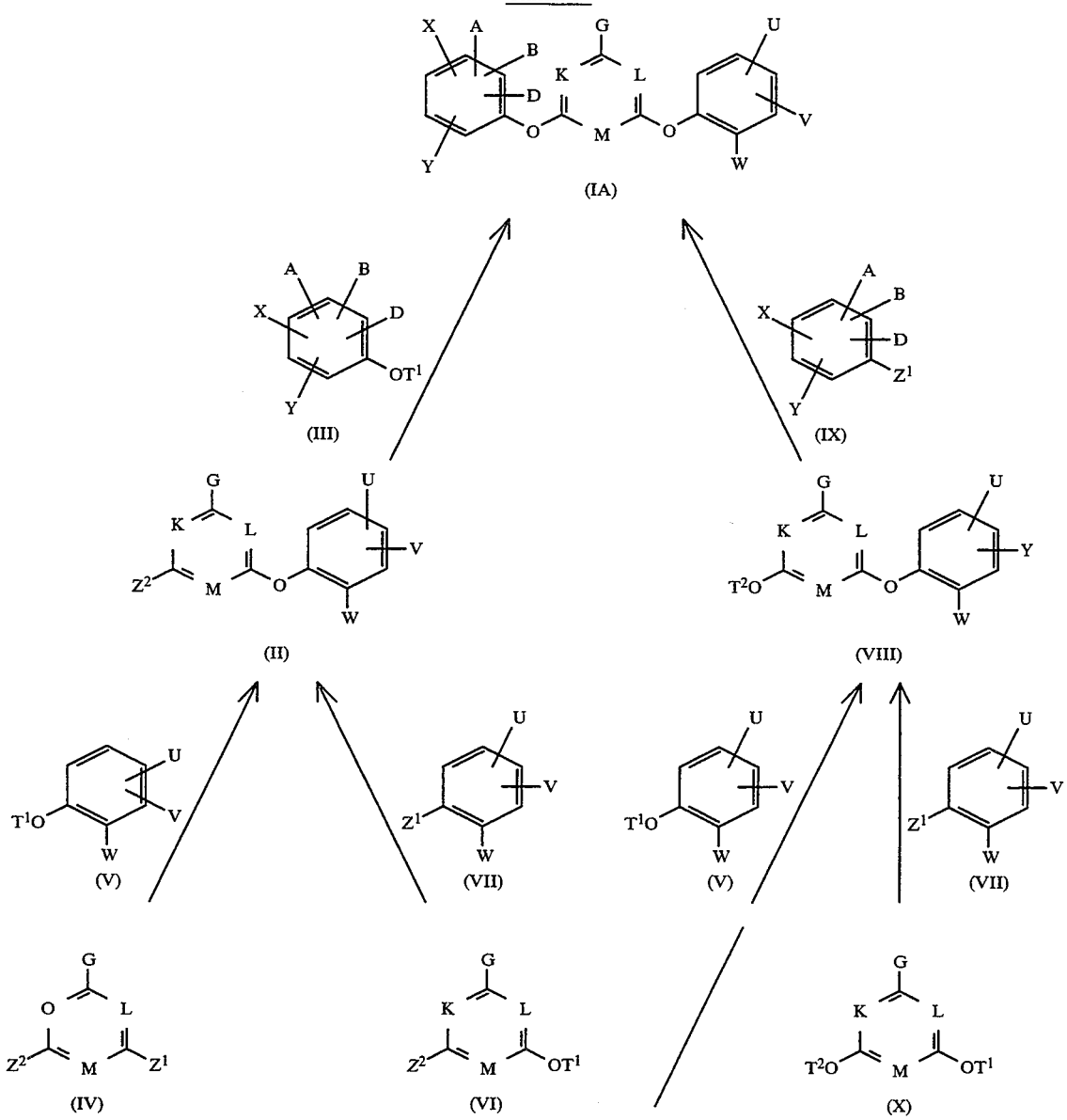

Scheme I

-continued
Scheme I

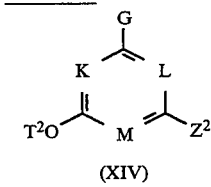

(XIV)

Scheme II

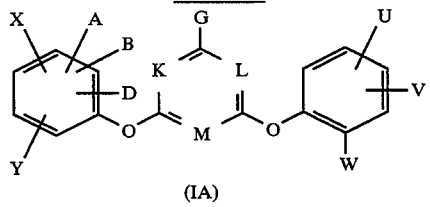

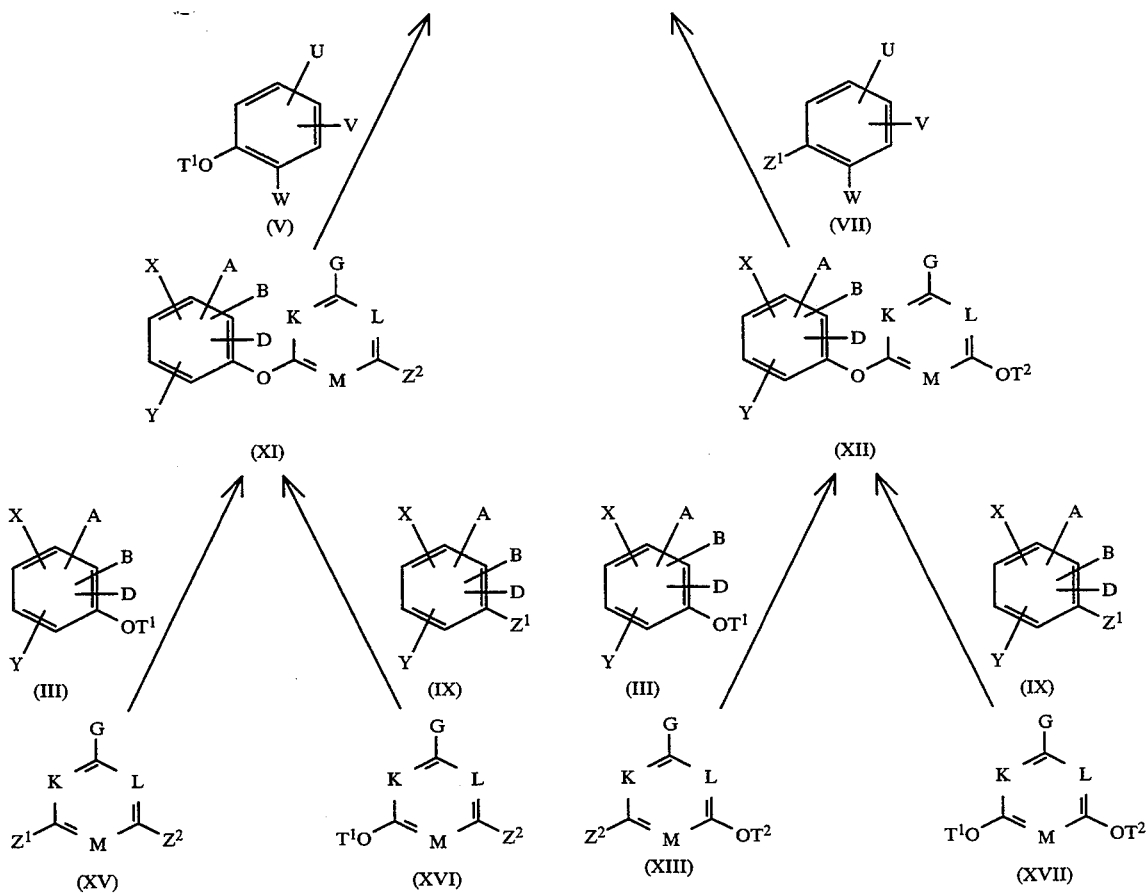

In a further aspect, the invention provides processes as hereindescribed for preparing the compounds of the invention.

The compounds of the invention are active fungicides and may be used to control one or more of the following pathogens:

*Pyricularia oryzae* on rice. *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants. *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines.

*Helminthosporium* spp., *Rhynchosporium* spp., *Septoria* spp., *Pyrenophora* spp., *Pseudocercosporella herpotrichoides* and *Gaeumannomyces graminis* on cereals.

*Cercospora arachidicola* and *Cercosporidium personata* on peanuts and other Cercospora species on other hosts, for example, sugar beet, bananas, soya beans and rice.

*Botrytis cinerea* (grey mould) on tomatoes, strawberries, vegetables, vines and other hosts.

*Alternaria* spp. on vegetables (e.g. cucumber), oilseed rape, apples, tomatoes and other hosts.

*Venturia inaequalis* (scab) on apples. *Plasmopara viticola* on vines.

Other downy mildews such as *Bremia lactucae* on lettuce, *Peronospora* spp. on soybeans, tobacco, onions and other hosts, *Pseudoperonospora humuli* on hops and *Pseudoperonospora cubensis* on cucurbits. *Phytophthora infestans* on potatoes and tomatoes and other *Phytophthora* spp, on vegetables, strawberries, avocado, pepper, ornamentals, tobacco, cocoa and other hosts.

*Thanatephorus cucumeris* on rice and other *Rhizoctonia* species on various hosts such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further, some of the compounds may be active as seed dressings against pathogens including *Fusarium* spp., *Septoria* spp., *Tilletia* spp,, (bunt, a seed-borne disease of wheat), *Ustilago* spp, and *Helminthosporium* spp. on cereals, *Rhizoctonia solani* on cotton and *Pyricularia oryzae* on rice.

The compounds may have systemic movement in plants. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropyl- naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1H-1,2,4-triazol-1-ylmethyl)butyronitrile, (RS)-4-chloro-N-(cyano(ethoxy)methyl)benzamide, (Z)-N-but-2-enyloxymethyl-2-chloro-2′,6′-diethylacetanilide, 1-(2-cyano-2-methoxyiminoacetyl)-3-ethyl urea, 1-[(2RS, 4RS; 2RS, 4RS)-4-bromo-2-(2,4-dichlorophenyl)tetrahydrofurfuryl]-1H-1,2,4-triazole, 3-(2,4-dichlorophenyl)-2-(1H-1,2,4-triazol-1-yl)-quinazolin-4(3H)-one, 3-chloro-4-[4-methyl-2-(1H-1,2,4-triazol-1-methyl)-1,3-dioxolan-2-yl]phenyl-4-chlorophenyl ether, 4-bromo-2-cyano-N,N-dimethyl-6-trifluoromethylbenzimidazole-1-sulphonamide, 4-chlorobenzyl N-(2,4-dichlorophenyl)-2-(1H-1,2,4-triazol-1-yl)thioacetamidate, 5-ethyl-5,8-dihydro-8-oxo(1,3)-dioxolo(4,5-g)quinoline-7-carboxylic acid, alpha-[N-(3-chloro-2,6-xylyl)-2-methoxyacetamido]-gammabutyrolactone, anilazine, benalaxyl, benomyl, biloxazol, binapacryl, bitertanol, blasticidin S, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1′-dioxide, dichlofluanid, dichlone, diclobutrazol, diclomezine, dicloran, dimethamorph, dimethirimol, diniconazole, dinocap, ditalimfos, dithianon, dodemorph, dodine, edifenphos, etaconazole, ethirimol, ethyl (Z)-N-benzyl-N-([methyl(-methylthioethylideneamino-oxycarbonyl)amino]-thio)-beta-alaninate, etridiazole, fenapanil, fenarimol, fenfuram, fenpiclonil, fenpropidin, fenpropimorph, fentin acetate, fentin hydroxide, flutolanil, flutriafol, fluzilazole, folpet, fosetylaluminium, fuberidazole, furalaxyl, furconazole-cis, guazatine, hexaconazole, hydroxyisoxazole, imazalil, iprobenfos, iprodione, isoprothiolane, kasugamycin, mancozeb, maneb, mepronil, metalaxyl, methfuroxam, metsulfovax, myclobutanil, N-(4-methyl-6-prop-1-ynylpyrimidin-2-yl)aniline, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, streptomycin, sulphur, techlofthalam, tecnazene, tebuconazole, tetraconazole, thiabendazole, thiophanatemethyl, thiram, tolclofosmethyl, triacetate salt of 1,1′-iminodi(octamethylene)-diguanidine, triadimefon, triadimenol, triazbutyl, triciyclazole, tridemorph, triforine, validamycin A, vinclozolin and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-dimethyl-2-oxo-1,2-dihydropyridine-3-carboxylic acid, methyl-3,6-dichloroanisate, abscisic acid, asulam, benzoylpropethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention. In the Examples, the term 'ether' refers to diethyl ether, anhydrous magnesium sulphate was used to dry solutions, and solutions were concentrated under reduced pressure. Reactions involving air- or water-sensitive intermediates were performed under an atmosphere of nitrogen and solvents were dried before use, where appropriate. Unless otherwise stated, chromatography was performed on a column of silica gel as the stationary phase. NMR data are selective; no attempt is made to list every absorption in all cases. $^1$H NMR spectra were recorded using CDCl$_3$-solutions on an instrument operating at 270 MHz, unless otherwise stated. The following abbreviations are used:

DMSO=dimethylsulphoxide
DMF=N,N-dimethyl formamide
NMR=nuclear magnetic resonance
IR=infrared
GC=Gas chromatography
TLC=Thin layer chromatography
s=singlet
d=doublet
m=multiplet
mp=melting point
ppm=parts per million

EXAMPLE 1

This example illustrates the preparation of (E)-methyl 2-[2-(4-phenoxypyrimidin-2-yloxy)phenyl]-3-methoxypropenoate (compound No. 1 of Table III).

To a suspension of sodium hydride (0.3 g,6.85 mmol, 50% dispersion in oil pre-washed with n-hexane) in dry DMF (4 ml) was added dropwise a solution of phenol (0.59 g, 6.23 mmol) in dry DMF (1 ml). The resulting mixture was stirred under an atmosphere of nitrogen until effervescence had ceased. The resulting mixture was diluted with dry DMF (3 ml) and then added dropwise to a stirred solution of 4-chloro-2-methylthiopyrimidine (1.00 g, 6.23 mmol) in dry DMF (3 ml) at 0° C. An exothermic reaction took place and the temperature of the reaction mixture rose to 5° C. After stirring under nitrogen for 30 minutes at 10° C., GC analysis indicated the formation of a single product (98.8%). The reaction mixture was diluted with water (15 ml) and extracted with ether (2×20 ml). The combined ether extracts were washed with 5% sodium hydroxide solution (2×15 ml) and brine (15 ml) and then dried. Evaporation of the solvent gave 2-methylthio-4-phenoxypyrimidine as a pale yellow oil (1.40 g, 94% pure by GC) which was used directly in the next stage. $^1$H NMR delta: 2.37 (3H, s)ppm.

To a stirred solution of 2-methylthio-4-phenoxypyrimidine (1.00 g, 4.59 mmol) in chloroform (15 ml) at −15° C. was added m-chloroperbenzoic acid (2.88 g, 9.17 mmol) in chloroform (35 ml). A white cloudy suspension formed. The reaction mixture was allowed to warm to room temperature and stirring continued for four hours. GC analysis indicated the formation of a single product (95%). The reaction mixture was washed with a saturated aqueous solution of sodium sulphite (2×25 ml), saturated sodium carbonate solution (2×25 ml) and water (25 ml). The chloroform solution was separated and dried. The solvent was evaporated to give a colourless oil which crystallised on cooling and scratching to afford 2-methanesulphonyl-4-phenoxypyrimidine as a white solid (1.05 g). Recrystallisation from chloroform:n-hexane gave a white finely divided powder, mp 113°–116° C., $^1$H NMR delta: 3.17 (3H,s)ppm; IR maxima (nujol) 1133, 1315 cm$^{-1}$.

To a solution of 2-methanesulphonyl-4-phenoxypyrimidine (200 mg, 0.80 mmol) in dry DMF (2 ml) at 0° C. under an atmosphere of nitrogen was added anhydrous potassium carbonate (110 mg, 0.80 mmol). A solution of (E)-methyl 2-(2-hydroxyphenyl)-3-methoxypropenoate (166 mg, 0.80 mmol; prepared as described in Example 3 of EP-A-0242081) in dry DMF (1 ml) was then added dropwise with stirring. The reaction mixture was allowed to rise to room temperature and then stirred over the weekend. The mixture was diluted with water (15 ml) and then extracted with ether (2×20 ml). The combined ether extracts were washed with brine, dried and evaporated to give a yellow oil. Chromatography (eluent ether:n-hexane, 5:1) gave a pale yellow cloudy oil, which on trituration with ether afforded the title compound as a white solid (0.10 g). Recrystallisation from ether:n-hexane gave a white solid (65 mg, 22% yield) mp 96°–7° C.; $^1$H NMR delta: 3.57 (3H, s); 3.70 (3H,s); 6.48. (1H,d); 7.12–7.45 (9H,m); 7.42 (1H, s); 8.29 (1H,d)ppm. IR maxima 1708, 1632 cm$^{-1}$.

EXAMPLE 2

This example illustrates the preparation of (E)-methyl 2-[2-(2-phenoxypyrimidin-4-yloxyphenyl]-3-methoxypropenoate (compound No. 1 of Table II).

To a stirred solution of 4-chloro-2-methylthiopyrimidine (10.00 g,62.3 mmol) in glacial acetic acid (50 ml) at 10°–15° C. was added a solution of potassium permanganate (12.50 g, 79.15 mmol) in water (100 ml). The reaction mixture was stirred overnight at room temperature, cooled to 5° C. and then treated with gaseous sulphur dioxide until the dark solution was decolourised. Water was added and the mixture extracted with chloroform. The combined organic layers were washed with saturated aqueous sodium bicarbonate solution and then water, and dried. Evaporation gave 4-chloro-2-methanesulphonylpyrimidine as a white solid (10.84 g),mp 91°–3° C. 4-Chloro-2-methanesulphonylpyrimidine (7.00 g,36.33 mmol) was treated with sodium phenoxide [from phenol (3.41 g,36.33 mmol) and sodium hydride (1.74 g,39.97 mmol,50% dispersion in oil)] in dry DMF (100 ml) at 0°–5° C. After 30 minutes, the starting material had been consumed (GC analysis). The reaction mixture was diluted with water and then extracted with ether (×2). The combined extracts were washed with 5% aqueous sodium hydroxide solution (×2) and brine, and then dried. Evaporation of the solvent gave a very pale yellow, mobile oil (5.35 g). Chromatography (eluent ether:n-hexane, 2:3) followed by crystallisation afforded 4-chloro-2-phenoxypyrimidine as a white solid (3.50 g, 84% pure by GC). Further chromatography yielded pure product (2.50 g, 33%), mp 59°–60° C.

To a stirred solution of 4-chloro-2-phenoxypyrimidine (2.00 g, 9.68 mmol) in dry DMSO (15 ml) and DMF (10 ml) at 10° C. under nitrogen was added dropwise a solution/suspension of sodium methanethiolate (0.77 g, 9.68 mmol) in dry DMSO (15 ml) and DMF (5 ml). After approximately one hour below 15° C., the reaction mixture was diluted with water and then extracted (×3) with ether. The combined ether extracts were washed with brine and then dried. Evaporation of the solvent gave 4-methylthio-2-phenoxypyrimidine as a thick, pale yellow oil (2.00 g,87% pure by GC) which was used in the next stage without further purification.

4-methylthio-2-phenoxypyrimidine (2.00 g, 7.96 mmol) in glacial acetic acid (12 ml) was treated with a solution of potassium permanganate (1.60 g, 10.11 mmol) in water (20 ml) as described above for 4-chloro-2-methylthiopyrimidine. Work up as before gave a pale yellow oil, which on trituration with ether and n-hexane afforded a pale yellow, slightly sticky powder (1.00 g). Recrystallisation from carbon tetrachloride/chloroform (trace)/n-hexane gave 4-methanesulphonyl-2-phenoxypyrimidine as a white powder (0.70 g, 35% yield) mp 86°–7° C., $^1$H NMR delta 3.19(3H,s)ppm; IR maxima (nujol) 1135, 1305 cm$^{-1}$.

To a solution of 4-methanesulphonyl-2-phenoxypyrimidine (300 mg, 1.20 mmol) in dry DMF (4 ml) was added anhydrous potassium carbonate (116 mg, 1.20 mmol). A solution of (E)-methyl 2-(2-hydroxyphenyl)-3-methoxypropenoate (0.250 g, 1.20 mmol, prepared as described in Example 3 of EP-A-0242081) in DMF was added and the reaction mixture was stirred at room temperature overnight. It was poured into water and extracted with ether. The ether extracts were washed with brine, dried and concentrated to give a yellow oil (0.48 g). Chromatography (eluent ether:n-hexane, 3:1) gave a white solid (0.34 g). Recrystallisation from carbon tetrachloride/dichloromethane (trace)/n-hexane gave the title compound as a white powder (0.31 g, 69% yield); mp 114°–115° C., $^1$H NMR (270 MHz) delta: 3.60 (3H, s); 3.74 (3H,s); 6.43 (1H,d); 7.11–7.42 (9H,m); 7.46 (1H, s); 8.28 (1H,d) ppm.

Mass spectrum m/e 378 (M+).

EXAMPLE 3

This example illustrates the preparation of (E)-methyl 2-[2-(6-(2-cyanophenoxy)pyrimidin-4-yloxy)phenyl]-3-methoxypropenoate (compound No. 9 of Table I).

To a solution of 4,6-dichloropyrimidine (0.76 g, 5.10 mmol) in dry DMF (4 ml) at 0° C. was added anhydrous potassium carbonate (0.70 g, 5.10 mmol). A solution of (E)-methyl 2-(2-hydroxyphenyl)-3-methoxypropenoate (0.53 g, 2.55 mmol, prepared as described in Example 3 of EP-A-0242081) in dry DMF (2 ml) was then added dropwise with stirring. After the addition was complete, the reaction mixture was allowed to warm to room temperature and stirring continued over the weekend. The reaction mixture was then diluted with water (15 ml) and extracted with ether (3×20 ml). The combined ether extracts were washed with brine and dried. Evaporation afforded a brown liquid (1.10 g) which was chromtographed (eluent ether:n-hexane, 3:2) to give (E)-methyl 2-[2-(6-chloropyrimidin-4-yloxy)phenyl]-3-methoxypropenoate as a thick, pale yellow oil (0.58, 71% yield) which was crystallised on standing. Recrystallisation from ether/dichloromethane (trace)/n-hexane at −78° C. gave the product as a white powder (0.25 g), mp 94°–5° C. In a separate preparation, 15 g of product was obtained from 4,6-dichloropyrimidine (15.90 g), (E)-methyl 2-(2-hydroxyphenyl)-3-methoxypropenoate (14.80 g) and anhydrous potassium carbonate (19.64 g).

(E)-Methyl 2-[2-(6-chlorpyridimin-4-yloxy)phenyl]-3-methoxypropenoate (1.50 g, 4.68 mmol) was heated overnight at 95°–100° C. with 2-cyanophenol (0.61 g, 5.15 mmol) and potassium carbonate (0.71 g, 5.15 mmol) in DMF (35 ml) in the presence of a catalytic amount of copper(I) chloride. The reaction mixture was cooled, diluted with water and then extracted with ether. The combined ether layers were washed with 2M sodium hydroxide solution and brine and then dried. Evaporation of the solvent gave a pale yellow oil (1.52 g). Recrystallisation from ether/dichlormethane/n-hexane gave the title compound as a pale yellow powder (1.20 g, 64% yield), mp 110°–111° C., $^1$H NMR delta: 3.63(3H, s); 3.74(3H,s); 6.42(1H,s); 7.19–7.47(6H, m); 7.50(1H,s); 7.62–7.75(2H,m); 8.40(1H,s)ppm. In a subsequent preparation of the title compound, recrystallisation gave a white crystalline solid, mp 118°–119° C.

EXAMPLE 4

This example illustrates the preparation of (E)-methyl 2-[2-(6-[2-hyudroxyphenoxy]pyrimidin-4-yloxy)-phenyl]-3-methoxypropenoate (compound No. 26 of Table I).

A mixture of catechol (6.6 g, 0.06 mol) and anhydrous potassium carbonate (8.28 g, 0.06 mol) in dry DMF (100 ml) was heated for one hour at 110° C. A catalytic amount of copper(I) chloride (0.2 g) was then added followed by a solution of (E)-methyl 2-[2-(6-chloropyrimidin-4-yloxy)phenyl]-3-methoxypropenoate (12.82 g, 0.04 mol, prepared as described in Example 3) in dry DMF (50 ml). The reaction mixture was heated at 110° C. for two hours, left to stand overnight, and then poured into water. The resulting mixture was extracted with ether ("extract A"). The remaining aqueous layer was acidified with concentrated hydrochloric acid and then extracted again with ether, these second extracts then being washed with water (×3), dried and evaporated to give a brown gum (6.78 g, "extract B"). "Extract A" was washed with dilute sodium hydroxide solution, and the resulting aqueous phase was acidifed with concentrated hydrochloric acid and extracted with ethyl acetate, this ethyl acetate extract then being washed with water, dried and evaporated to give a brown gum (6.68 g, "extract C"). Extracts "B" and "C" were combined and then chromatographed (eluent ether) to afford the title compound (7.8 g, 49.5% yield) as a yellow solid which was identical to a sample prepared earlier on a smaller scale, mp 159°–161° C., IR max. 3100, 1712, 1642 cm$^{-1}$; $^1$H NMR delta: 3.61 (3H, s); 3.75 (3H, s); 6.30 (1H, s); 6.52 (1H, s); 6.91–6.97 (1H, m); 7.05–7.21 (4H, m); 7.26–7.48 (3H, m); 7.45 (1H, s); 8.44 (1H, s)ppm.

EXAMPLE 5

This example illustrates the preparation of (E)-methyl 2-[2-(6-(2-methoxyphenoxy)pyrimidin-4-yloxy)phenyl]-3-methoxypropenoate (compound No. 29 of Table I).

To a stirred solution of (E)-methyl 2-[2-(6-[2-hydroxyphenoxy]pyrimidin-4-yloxy)phenyl]-3-methoxypropenoate (0.50 g, 1.27 mmol, prepared as described in Example 4) in dry DMF (15 ml) at 0° C. was added anhydrous potassium carbonate (0.17 g, 1.27 mol) and methyl iodide (0.22 g, 1.52 mmol). The reaction mixture was allowed to warm to room temperature, stirred for two hours and then left to stand over the weekend. The mixture was diluted with water (20 ml) and then extracted with ether (3×25 ml). The combined ether extracts were washed with dilute sodium hydroxide solution (2×20 ml) and brine (20 ml) and then dried. Evaporation gave a pale pink foam (0.36 g) which was chromatographed (eluent ether-hexane, 7:1) to afford the title compound as a white foam (0.21 g, 40% yield); $^1$H NMR delta, 3.60 (3H, s); 3.76 (3H, s); 3.78 (3H, s); 6.25 (1H, s); 6.95–7.52 (8H, m); 7.49 (1H, s); 8.42 (1H, s)ppm.

In an alternative preparation, (E)-methyl 2-[2-(6-chloropyrimidin-4-yloxy)phenyl]-3-methoxypropenoate (1.00 g, 3.12 mmol, prepared as described in Example 3) was treated with sodium methanethiolate (1.09 g, 15.60 mmol) at room temperature in chloroform (15 ml) and water (10 ml) in the presence of a catalytic amount of tetrabutylammonium bromide. After stirring overnight, the chloroform layer was separated and the remaining aqueous layer was further extracted with chloroform. The combined chloroform layers were washed with water, dried and evaporated to give an orange oil (1.56 g). Chromatography (eluent ether-hexane, 2:1) gave (E)-methyl 2-[2-(6-methylthiopyrimidin-4-yloxy)-phenyl]-3-methoxypropenoate as a pale yellow oil (0.92 g, 89% yield); $^1$H NMR delta: 2.52 (3H, s); 3.59 (3H, s); 3.73 (3H, s); 6.55 (1H, s); 7.17 (1H, d); 7.20–7.55 (3H, m); 7.45 (1H, s); 8.57 (1H, s)ppm.

The product (0.20 g, 0.6 mmol) was stirred overnight with meta-chloroperbenzoic acid (0.38 g of 55% pure material) in chloroform (25 ml) at room temperature. Work-up gave the corresponding sulphone (0.26 g, 94% pure by gc) as a thick, colourless oil which was used directly in the next stage without further purification, $^1$H NMR delta: 3.25 (SO$_2$CH$_3$), 7.45 (olefinic proton)ppm.

To a stirred solution of the sulphone (0.24 g) in dry DMF (6 ml) was added anhydrous potassium carbonate (0.091 g) and a solution of 2-methoxyphenol (0.082 g) in dry DMF (2 ml). The reaction mixture was stirred for four hours and then overnight at room temperature, diluted with water (15 ml) and then extracted with ether (3×20 ml). The combined ether extracts were washed with dilute sodium hydroxide solution (2×15 ml) and brine (15 ml) and then dried. Evaporation gave a thick, pale yellow oil (0.25 g). Chromatography (eluent ether-hexane, 7:1) afforded the title compound as a sticky, white foam (0.17 g, 63% yield), $^1$H NMR as before.

EXAMPLE 6

This example illustrates the preparation of (E)-methyl 2-[2-(6-(2-thiocarboxamidophenoxy)pyrimidin-4-yloxy)phenyl]-3-methoxypropenoate (Compound No. 59 of Table I).

Excess hydrogen sulphide gas was bubbled through a stirred solution of (E)-methyl 2-[2-(6-(2-cyanophenoxy)pyrimidin-4-yloxy)phenyl-3methoxypropenoate (2.09 g, 15.19 mmol, prepared as described in Example 3) and triethylamine (0.52 g) in dry pyridine (45 ml) at 50° C. After 4½ hours at 50° C. and one week at room temperature, excess hydrogen sulphide was removed by passing air through the reaction mixture. The resulting brown solution was evaporated and azeotroped with toluene (2×50 ml) to give a brown oil, which was triturated with water (3×40 ml). The residue was chromatographed (eluent acetone-hexane, 2:3) to afford a pale yellow oil (0.79 g). Trituration with hexane gave the title compound as a pale orange powder (0.68 g, 30% yield) mp 125°–128° C. A sample prepared subsequently had mp 131°–3° C., $^1$H NMR delta: 3.63 (3H, s); 3.78 (3H, s); 6.27 (1H, s); 7.18 (1H, d); 7.10–7.60 (6H, m); 7.49 (1H, s); 7.71 (1H, s); 7.91 (1H, s); 8.05 (1H, dd); 8.39 (1H, s)ppm.

EXAMPLE 7

This example illustrates the preparation of:

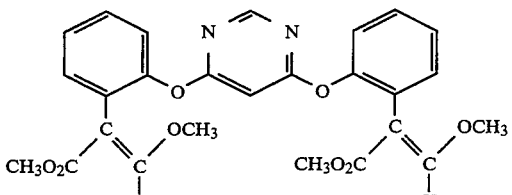

(Compound No. 123 of Table I)

and:

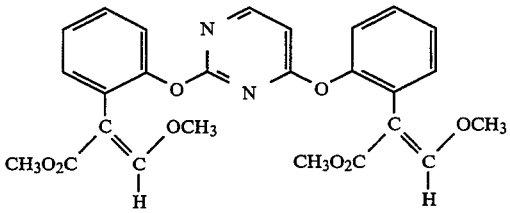

(Compound No. 123 of Table II)

To a stirred mixture of (E)-methyl 2-(2-hydroxyphenyl)-3-methoxypropenoate (2.43 g, prepared as described in Example 3 of EP-A-0242081) and anhydrous potassium carbonate (1.61 g) in dry DMF (25 ml) at 0° C., was added dropwise a solution of 2,4,6-trichloropyrimidine in dry DMF (5 ml). The reaction mixture was stirred for 30 minutes at 0° C. and over the weekend at room temperature and then poured into water and extracted with ether (×3). The combined ether extracts were washed with dilute sodium hydroxide solution and water (×3) and then dried. Evaporation afforded an orange gum (2.62 g) which was chromatographed (eluent ether-hexane mixtures) to give (E)-methyl 2-[2-(2,4-dichloropyrimidin-6-yloxy)-phenyl]-3-methoxypropenoate (0.65 g) as an off-white solid, mp 88°–90° C., and a mixture (1.07 g, approx 1:1) containing:

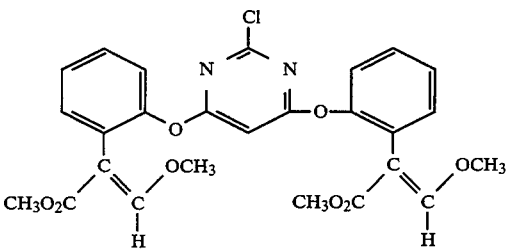

and:

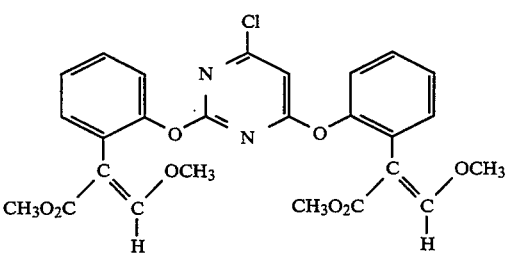

To a stirred solution of part of this mixture (0.97 g) in THF (25 ml) were added 5% Pd/C catalyst (0.11 g) and then, dropwise over 5 minutes, sodium hypophosphite (0.405 g) in water (5 ml). After stirring at room temperature for two hours, the temperature was raised to 60° C. and additional portions of sodium hypophosphite (0.41 g) in water (5 ml) (after a further 30 minutes) and potassium carbonate (0.76 g) and palladium catalyst (0.11 g) (after a further one hour) were added. When the starting materials had been consumed (GC and TLC analysis) the reaction mixture was filtered through celite, washing the plug with ether and water. The layers of the filtrate were separated and the aqueous layer was extracted with more ether. The combined ether layers were washed with water ($\times 2$), dried and evaporated to give a white foam (0.78 g). Chromatography (eluent ether) gave compound No. 123 of Table I, eluted first, as a white solid (0.34 g); mp 130°–131° C.; IR max. 1705, 1693, 1636 cm$^{-1}$; $^1$H NMR delta: 3.59 (6H, s); 3.75 (6H, s); 6.16 (1H, s); 7.14–7.18 (2H, m); 7.24–7.41 (6H, m); 7.45 (2H, s); 8.39 (1H, s) ppm; and compound No. 123 of Table II as a white foam (0.23 g); mp 60°–70° C.; IR max. 1706, 1632cm$^{-1}$; $^1$H NMR delta: 3.56 (3H, s) 3.58 (3H, s); 3.70 (3H, s); 3.74 (3H, s); 6.34–6.37 (1H, d); 7.15–7.35 (8H, m); 7.44 (1H, s); 7.47 (1H, s); 8.21–8.24 (1H, s)ppm.

EXAMPLE 8

This example illustrates the preparation of (E)-methyl 2-[2-(4-fluoropyrimidin-6-yloxy)phenyl]-3-methoxypropenoate, an intermediate for the synthesis of compounds of the invention.

A mixture of 4,6-dichloropyrimidine (6.50 g), sulphur tetrafluoride (20.8 g) and Arcton 113 (35 ml) was heated at 50° C. with stirring in a 100 ml Monel reactor for 3.3 hours. The temperature was increased to 100° C. over 25 minutes and maintained at 100° C. for a further 3 hours. The temperature was increased to 151° C. over 20 minutes and maintained at 151° C. for 3 hours. The vessel was then allowed to cool to room temperature. The reaction mixture was poured into saturated sodium hydrogen carbonate solution and extracted with dichloromethane. A sticky solid was observed at the interface and was removed by filtration. The layers were then separated. The organic layer was washed with water, and then distilled at atmospheric pressure to remove the dichloromethane. 4,6-Difluoropyrimidine was isolated by distillation in vacuo (50° C./100 mmHg) as a light yellow oil (400 mg; 7.3% yield); $^1$H NMR delta: 6.61 (1H, s); and 8.69 (1H, s)ppm.

To a solution of (E)-methyl 2-(2-hydroxyphenyl)-3-methoxypropenoate (359 mg, 1.724 mmol, prepared as described in Example 3 of EP-A-0242081) in dry DMF (3 ml) at room temperature was added dry potassium carbonate (476 mg, 3.45 mmol) in one portion. The reaction mixture was stirred at room temperature for 20 minutes, then a solution of 4,6-difluoropyrimidine (200 mg) in dry DMF (2 ml) was added, via syringe, over approximately 1 minute. The reaction mixture was then stirred for a further 20 hours at room temperature, poured into water (20 ml) and extracted with ethyl acetate ($4 \times 30$ ml). The combined extracts were washed successively with water ($2 \times 100$ ml) and with saturated brine ($1 \times 100$ ml), then dried and concentrated to give the title compound as a sticky yellow oil (464 mg; 88% yield); $^1$H NMR delta: 3.59 (3H, s); 3.73 (3H, s); 6.32 (1H, s); 7.16–7.43 (4H, m); 7.45(1H, s); 8.51 (1H, d)ppm.

The following are examples of compositions suitable for agricultural and horticultural purposes which can be formulated from the compounds of the invention. Such compositions form another aspect of the invention. Percentages are by weight.

EXAMPLE 9

An emulsifiable concentrate is made up by mixing and stirring the ingredients until all are dissolved.

| | |
|---|---|
| Compound No. 9 of Table I | 10% |
| Benzyl alcohol | 30% |
| Calcium dodecylbenzenesulphonate | 5% |
| Nonylphenolethoxylate (13 mole ethylene oxide) | 10% |
| Alkyl benzenes | 45% |

EXAMPLE 10

The active ingredient is dissolved in methylene dichloride and the resultant liquid sprayed on to the granules of attapulgite clay. The solvent is then allowed to evaporate to produce a granular composition.

| | |
|---|---|
| Compound No. 9 of Table I | 5% |
| Attapulgite granules | 95% |

EXAMPLE 11

A composition suitable for use as a seed dressing is prepared by grinding and mixing the three ingredients.

| | |
|---|---|
| Compound No. 9 of Table I | 50% |
| Mineral oil | 2% |
| China clay | 48% |

EXAMPLE 12

A dustable powder is prepared by grinding and mixing the active ingredient with talc.

| | |
|---|---|
| Compound No. 9 of Table I | 5% |
| Talc | 95% |

EXAMPLE 13

A suspension concentrate is prepared by ball milling the ingredients to form an aqueous suspension of the ground mixture with water.

| | |
|---|---|
| Compound No. 9 of Table I | 40% |
| Sodium lignosulphonate | 10% |
| Bentonite clay | 1% |
| Water | 49% |

This formulation can be used as a spray by diluting into water or applied directly to seed.

EXAMPLE 14

A wettable powder formulation is made by mixing together and grinding the ingredients until all are thoroughly mixed.

| | |
|---|---|
| Compound No. 9 of Table I | 25% |
| Sodium lauryl sulphate | 2% |
| Sodium lignosulphonate | 5% |
| Silica | 25% |

-continued

| | |
|---|---|
| China clay | 43% |

EXAMPLE 15

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4=no disease
3=trace −5% of disease on untreated plants
2=6–25% of disease on untreated plants
1=26–59% of disease on untreated plants
0=60–100% of disease on untreated plants
The results are shown in Table V.

TABLE V

| COMPOUND NO | TABLE NO | *PUCCINIA RECONDITA* (WHEAT) | *ERYSIPHE GRAMINIS* (BARLEY) | *VENTURIA INAEQUALIS* (APPLE) | *PYRICULARIA ORYZAE* (RICE) |
|---|---|---|---|---|---|
| 1 | I | 4 | 4 | 4 | 3 |
| 2 | I | 4 | 4 | 4 | 3 |
| 3 | I | 4 | 4 | 4 | 4 |
| 5 | I | 4 | 4 | 4 | 4b |
| 8 | I | 4 | 4 | 4 | 3 |
| 9 | I | 4c | 4 | 4 | 4 |
| 10 | I | 4 | 4 | 4 | 3 |
| 11 | I | 4 | 4 | 4 | 3 |
| 13 | I | 4a | 4 | 4 | 4 |
| 14 | I | 4 | 4 | 4 | 4 |
| 15 | I | 4 | 4 | 4 | 4 |
| 16 | I | 4 | 4 | 4 | 3 |
| 26 | I | 4 | 3 | 4 | 0 |
| 29 | I | 4 | 4 | 4 | 3 |
| 30 | I | 4 | 4 | 4 | 4 |
| 31 | I | 4 | 4 | 4 | 3 |
| 32 | I | 4 | 4 | 4 | 4 |
| 34 | I | 3 | 2 | 4 | 2 |
| 35 | I | 3 | 4 | 4 | 0 |
| 40 | I | 4 | 4 | 4 | 3 |
| 43 | I | 4 | 4 | 4 | 3 |
| 44 | I | 4 | 4 | 4 | 2 |
| 46 | I | 4 | 4 | 4 | 1 |
| 49 | I | 4 | 4 | 4 | 4 |
| 51 | I | 4 | 4 | 4 | 0 |
| 59 | I | 4a | 4a | 4a | 2a |
| 62 | I | 4 | 4 | 4 | 3 |
| 63 | I | 4 | 4 | 4 | 4 |
| 64 | I | 4 | 4 | 4 | 4 |
| 76 | I | 4 | 4 | 4 | 3 |
| 77 | I | 4 | 4 | 4 | 4 |
| 80 | I | 4 | 4 | 4 | 4 |
| 81 | I | 4 | 4 | 4 | 3 |
| 82 | I | 4 | 4 | 4 | 4 |
| 101 | I | 4 | 4 | 4 | 2 |
| 102 | I | 4 | 4 | 4 | 4 |
| 103 | I | 4 | 4 | 4 | 4 |
| 104 | I | 4 | 4 | 4 | 4 |
| 105 | I | 4 | 4 | 4 | 4 |
| 106 | I | 4 | 4 | 4 | 4 |
| 107 | I | 4 | 4 | 4 | 4 |
| 108 | I | 4 | 4 | 4 | 4 |
| 109 | I | 4 | 4 | 4 | 4 |
| 110 | I | 4 | 4 | 4 | 4 |
| 111 | I | 4 | 4 | 3 | — |
| 112 | I | 4a | 3a | 4a | — |
| 113 | I | 4 | 4 | 4 | 4 |
| 114 | I | 4 | 4 | 4a | 4 |
| 115 | I | 4 | 4 | 4 | 4 |
| 116 | I | 4 | 4 | 4 | 4 |

TABLE V-continued

| | | | | | |
|---|---|---|---|---|---|
| 117 | I | 4 | 4 | 4 | 3 |
| 118 | I | 4a | 4a | 0a | — |
| 119 | I | 4 | 4 | 4 | 2 |
| 121 | I | 4a | 3a | 4a | 3a |
| 122 | I | 4 | 4 | 4 | 4 |
| 161 | I | 4 | 4 | 4 | 3 |
| 1 | II | 4 | 4 | 4 | 2b |
| 1 | III | 3b | 4b | 4b | 3b |
| 9 | III | 4a | 3a | — | 1a |

| COMPOUND NO | TABLE NO | CERCOSPORA ARACHIDICOLA (PEANUT) | PLASMOPARA VITICOLA (VINE) | PHYTOPHTHORA INFESTANS (TOMATO) |
|---|---|---|---|---|
| 1 | I | 4 | 4 | 3 |
| 2 | I | 4 | 4 | 4 |
| 3 | I | 4 | 4 | 4 |
| 5 | I | 4 | 4 | 4 |
| 8 | I | 4 | 4 | 4 |
| 9 | I | 4 | 4 | 4 |
| 10 | I | 4 | 4 | 4 |
| 11 | I | 4 | 4 | 4 |
| 13 | I | 4 | 4 | 4 |
| 14 | I | 4 | 4 | 4 |
| 15 | I | 4 | 4 | 4 |
| 16 | I | 0 | 4 | 4 |
| 26 | I | 2 | 4 | 4 |
| 29 | I | 4a | 4 | 4 |
| 30 | I | 4 | 4 | 4 |
| 31 | I | 4 | 4 | 4 |
| 32 | I | 4 | 4 | 4 |
| 34 | I | 4 | 4 | 0 |
| 35 | I | 4 | 4 | 2 |
| 40 | I | 4 | 4 | 4 |
| 43 | I | 4 | 4 | 4 |
| 44 | I | 4 | 4 | 4 |
| 46 | I | 2 | 4 | 4 |
| 49 | I | 4 | 4 | 4 |
| 51 | I | 4 | 4 | 4 |
| 59 | I | 4a | 4a | 4a |
| 62 | I | 4 | 4 | 4 |
| 63 | I | 4 | 4 | 4 |
| 64 | I | 4 | 4 | 4 |
| 76 | I | 4 | 4 | 3 |
| 77 | I | — | 4 | 4 |
| 80 | I | 4 | 4 | 3 |
| 81 | I | 4 | 4 | 4 |
| 82 | I | 4 | 4 | 4 |
| 101 | I | 4 | 4 | 4 |
| 102 | I | 4 | 4 | 4 |
| 103 | I | 4 | 4 | 3 |
| 104 | I | 4 | 4 | 4 |
| 105 | I | 4 | 4 | — |
| 106 | I | 4 | 4 | 4 |
| 107 | I | 4 | 4 | 4 |
| 108 | I | 4 | 4 | 4 |
| 109 | I | 4 | 4 | 4 |
| 110 | I | 4 | 4 | 4 |
| 111 | I | — | 4 | 4 |
| 112 | I | 4a | — | 0a |
| 113 | I | 4 | 4 | 3 |
| 114 | I | 4 | 4a | 3a |
| 115 | I | 4 | 4 | 3 |
| 116 | I | — | 4 | 4 |
| 117 | I | — | 4 | 4 |
| 118 | I | — | 4a | 3a |
| 119 | I | — | 4 | 1 |
| 121 | I | — | 4a | 0a |
| 122 | I | — | 4 | 4 |
| 161 | I | 4 | 4 | 4 |
| 1 | II | 4 | 4 | 3 |
| 1 | III | 4b | 4b | 4b |
| 9 | III | 4a | 4a | 3a | a 10 ppm foliar spray only
b 25 ppm foliar spray only
c 5 ppm foliar spray only
— No result

We claim:
1. The compound (E)-methyl 2-(2-[6-(2-cyanophenoxy)pyrimidin-4-yloxy]-phenyl)-3-methoxypropenoate having the formula:

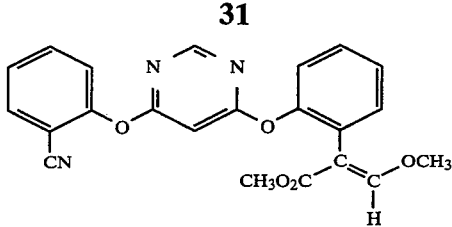

2. A fungicidal composition comprising a fungicidally effective amount of a compound according to claim 1 and a fungicidally acceptable carrier or diluent therefor.

3. A method of combating fungi which comprises applying to plants, to the seeds of plants or to the locus of the plants or seeds a compound according to claim 1.

4. The method of claim 3 wherein said compounds is used for combating fungi on wheat, turf, peanut, vine, potato, tomato, sugar beet, cotton or rice.

5. The method of claim 3 wherein said compounds is used for the control of one or more of the following fungal pathogens: *Puccinia recondita, Erysiphe graminis, Uncinula necator*, Helminthosporium spp., Septoria spp., *Gaeumannomyces graminis, Cercospora arachidicola, Cercosporidium personata, Botrytis cinerea*, Alternaria spp., *Plasmopara viticola, Phytophthora infestans*, Fusarium spp., *Rhizoctonia solani* and *Pyricularia oryzae.*

6. The method of claim 3 wherein said compound is used for the control of *Puccinia recondita, Erysiphe graminis* or Rhizoctonia spp. on wheat, *Uncinula necator, Botrytis cinerea* or *Plasmopara viticola* on vines, Septoria spp., Fusarium spp. or *Gaeumannomyces graminis* on cereals, *Cercospora arachidicola* or *Cercosporidium personata* on peanuts, Alternaria spp., *Botrytis cinerea* or *Phytophthora infestans* on tomatoes, *Phytophthora infestans* on potatoes, Rhizoctonia spp. on turf, *Rhizoctonia solani* on cotton or *Pyricularia oryzae* on rice.

* * * * *